United States Patent
Nelson

(10) Patent No.: US 11,041,141 B2
(45) Date of Patent: Jun. 22, 2021

(54) CULTURE INSERT ASSEMBLY AND SYSTEM FOR CULTURE, TRANSFER, AND ANALYSIS

(71) Applicant: DRAMEDICA, L.L.C., Raleigh, NC (US)

(72) Inventor: M. Bud Nelson, Raleigh, NC (US)

(73) Assignee: Dramedica LLC, Raleigh, NC (US)

(*) Notice: Subject to any disclaimer, the term of this patent is extended or adjusted under 35 U.S.C. 154(b) by 610 days.

(21) Appl. No.: 15/759,897

(22) PCT Filed: Oct. 22, 2016

(86) PCT No.: PCT/US2016/058347
§ 371 (c)(1),
(2) Date: Mar. 14, 2018

(87) PCT Pub. No.: WO2017/074829
PCT Pub. Date: May 4, 2017

(65) Prior Publication Data
US 2018/0298320 A1 Oct. 18, 2018

Related U.S. Application Data

(60) Provisional application No. 62/246,378, filed on Oct. 26, 2015.

(51) Int. Cl.
*C12M 1/12* (2006.01)
*C12M 3/00* (2006.01)

(52) U.S. Cl.
CPC ............ *C12M 25/04* (2013.01); *C12M 21/08* (2013.01)

(58) Field of Classification Search
CPC .............................. C12M 25/04; C12M 21/08
See application file for complete search history.

(56) References Cited

U.S. PATENT DOCUMENTS

| | | | |
|---|---|---|---|
| 5,139,951 A * | 8/1992 | Butz | C12M 23/00 422/552 |
| 2003/0215940 A1 | 11/2003 | Lacey | |
| 2004/0091397 A1* | 5/2004 | Picard | B01L 3/50853 422/400 |
| 2005/0221274 A1 | 10/2005 | Negulescu et al. | |
| 2006/0172412 A1* | 8/2006 | Perrier | C12M 23/20 435/297.5 |
| 2008/0003670 A1 | 1/2008 | Martin et al. | |
| 2010/0047907 A1 | 2/2010 | Li et al. | |
| 2014/0363883 A1 | 12/2014 | Hayes et al. | |

FOREIGN PATENT DOCUMENTS

| | | |
|---|---|---|
| EP | 2 230 296 | 9/2010 |
| WO | WO2006/131123 | 12/2006 |
| WO | WO2011/127945 | 10/2011 |

OTHER PUBLICATIONS

Jun. 5, 2019 (EP) Extended European Search Report App. 16860554.1.

* cited by examiner

*Primary Examiner* — William H. Beisner
*Assistant Examiner* — Danielle B Henkel

(57) ABSTRACT

Provided is a culture system comprising a base comprising a multiwell plate; a transwell-like type insert plate comprising a plurality of culture insert assemblies, wherein each culture insert assembly comprises a culture surface element that is removably mounted to a culture insert body; and a cover designed to fit over the transwell-like type insert plate.

17 Claims, 8 Drawing Sheets

CULTURE INSERT ASSEMBLY AND SYSTEM FOR CULTURE, TRANSFER, AND ANALYSIS

FIELD OF THE INVENTION

This invention relates to a system for culturing cells or tissues in vitro, as well for facilitating the development of such cultures and subsequent analysis of the cultures.

BACKGROUND OF THE INVENTION

There is an international emphasis on development and implementation of research and development methods that avoid the use of live animals. A major alternative to in vivo animal testing is in vitro culture techniques. In that regard, in vitro assays and systems are being developed in efforts to mimic or represent biological systems of humans. Such assays and systems typically depend on in vitro culture of representative cells or tissue. Regarding the latter, success has been demonstrated for bioprinting functional human tissues. In the bioprinting process, biological components of tissue (e.g., structural components, tissue components, and various cell types) are strategically layered onto a matrix to create a functional tissue. There is a need for devices, systems, and technology which can provide more effective use of in vitro assays and biological systems in their implementation as substitutes for in vivo animal testing.

SUMMARY OF THE INVENTION

The invention relates to a culture system that utilizes a culture insert assembly that comprises a removably attachable culture surface element on which cells or tissues are cultured. A plurality of culture surface elements are removably attached to culture insert bodies which are integrally formed as part of a transwell-like type insert plate. A culture insert assembly comprises a culture surface element removably attached to a culture insert body. The removably attachable culture surface elements comprise movable units that can be transferred between a transwell-like type insert plate and a transfer plate (i.e., from a transwell-like type insert plate to a transfer plate, or from a transfer plate to a transwell-like type insert plate, depending on the purpose of use by a user). Also provided is a transfer plate for facilitating (a) removal of a plurality of culture surface elements, (b) storage or shipping of a plurality of culture surface elements comprising one or more culture components applied thereon, and (c) manipulations of the culture surface (e.g., deposition of cells, tissues, or biological components for culturing) or of the cells or tissues (e.g., processing for imaging, and imaging) applied to the plurality of culture surface elements removably attached to the transfer plate.

As a first aspect of the invention, provided is a culture system adapted to provide for more effective manual and automatic handling of culture inserts, and particularly for manipulation of culture components (e.g., cells and/or tissues) present on the culture surface of a culture insert.

Another aspect of the invention is to provide a culture insert assembly having a culture surface element which is removably attachable to the culture insert assembly, wherein the culture surface element can facilitate a process of manufacturing or use, such as for deposition of cells or bioprinting of tissues.

Another aspect of the invention is to provide a culture insert assembly having a culture surface element which is detachable from a culture insert assembly, in a process of transferring the culture surface element to a transfer plate that also facilitates biological characterization, analysis, or further manipulation of culture components present on the surface for growth provided on the culture surface element.

Also provided is a transwell-like type insert plate that comprises a plurality of culture insert assemblies, and wherein a culture insert assembly is comprised of a culture insert body and a culture surface element, wherein the culture surface element is removably attachable to the culture insert body.

Also provided is a method of transferring a plurality of culture surface elements from a transwell-like type insert plate to a transfer plate, wherein the transwell-like type insert plate comprises a plurality of culture insert assemblies, and wherein removably attached to a culture insert assembly is a culture surface element, the method comprising: (a) spatially aligning a plurality of culture surface elements with one or more openings of the transfer plate; (b) inserting one or more engagement elements of each culture surface element, of the plurality of culture surface elements, into one or more guiding elements of the transfer plate, and engaging the one or more guiding elements with the one or more engagement elements, in securedly engaging or removably fixedly engaging the plurality of culture surface elements to the transfer plate; (c) disengaging or removing the plurality of culture surface elements from the transwell-like type insert plate; wherein the plurality culture surface elements are engaged with or attached to the transfer plate.

Provided is a method of transferring a plurality of culture surface elements from a transfer culture assembly to a transwell-like type insert plate, wherein the transfer culture assembly comprises a plurality of culture surface elements removably attached to a transfer plate, the method comprising: (a) aligning one or more attachment elements of each culture surface element, of a plurality of culture surface elements, with one or more attachment elements a culture insert body, of a plurality of culture insert bodies, of the transwell-like type insert plate; (b) contacting the one or more attachment elements of each culture surface element, of a plurality of culture surface elements, with one or more attachment elements of a culture insert body, of a plurality of culture insert bodies, in securedly engaging or removably fixedly engaging the plurality of culture surface elements to the transwell-like type insert plate; (c) disengaging or removing the plurality of culture surface elements from the transfer plate; wherein the plurality culture surface elements are engaged with or attached to the transwell-like type insert plate.

It is an important advantage of the invention that the plurality of culture surface elements can be handled together, and moved together, whether manually or using an automated system.

DETAILED DESCRIPTION OF THE INVENTION

The invention relates to a culture system that utilizes a culture insert assembly that comprises a removably attachable culture surface element on which cells or tissues are cultured. A plurality of culture surface elements is removably attached to corresponding culture insert bodies which are integrally formed as part of a transwell-like type insert plate. A culture insert assembly comprises a culture surface element removably attached to a culture insert body. The removably attachable culture surface elements comprise movable units that can be transferred between a transwell-like type insert plate and a transfer plate (i.e., from a transwell-like type insert plate to a transfer plate, or from a transfer plate to a transwell-like type insert plate) depending on the purpose of use by a user. Also provided is a transfer plate for facilitating (a) removal of a plurality of culture surface elements from a transwell-like type insert plate comprising a plurality of culture insert assemblies, (b) storage or shipping of a plurality of culture surface elements removably attached to a transfer plate, and (c) manipulations of the culture surface of (e.g., deposition of cells, tissues, or biological components for culturing), or the cells or tissues (e.g., processing for imaging, and imaging) applied to, a plurality of culture surface elements removably attached to a transfer plate.

Figure 1:
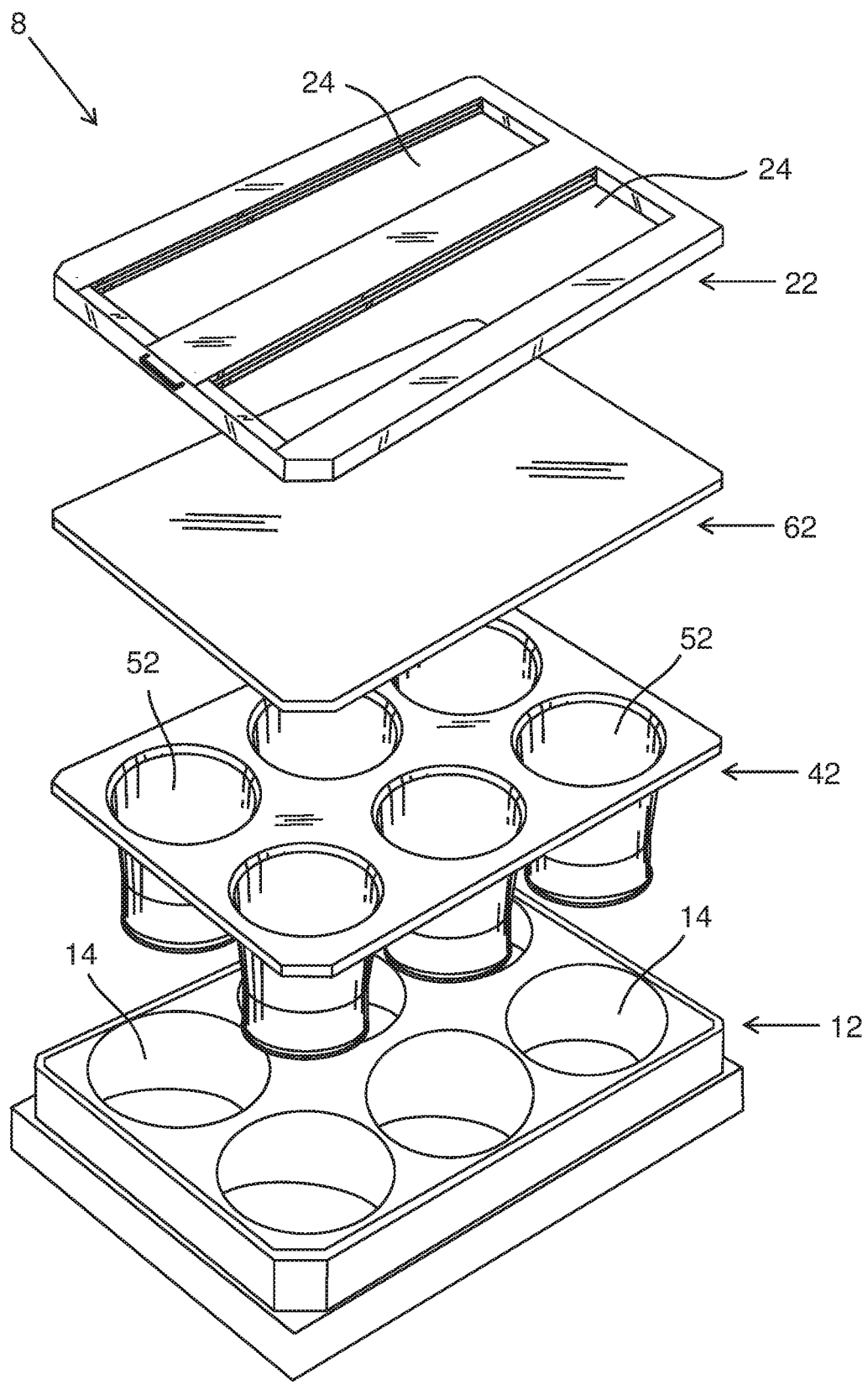
FIG. 1 schematically shows a culture system according to the invention.

As illustrated in FIG. 1, the culture system 8 of the invention is provided which includes a base 12 comprising a multiwell plate for culturing cells or tissues; a transwell-like type insert plate 42 comprising a plurality of culture insert assemblies 52, wherein each culture insert assembly comprises a culture surface element that is removably mounted to a culture insert body; and a cover or lid 62 designed to fit over the transwell-like type insert plate. The culture system 8 may further comprise a transfer plate 22 comprising a plurality of openings 24. The multiwell plate 12 comprises a plurality of openings (wells) 14 such as, for example, 2, 4, 6, 8, 12, 16, 24, 36, 48, or 96 openings, or other number as desired by a user of the system. Transfer plate 22 comprises a plurality of openings 24 substantially extending and positioned along the length of transfer plate 22. In one aspect, the culture insert assemblies 52 of the transwell-like type insert plate 42, and the wells 14 in multiwell plate 12, would desirably correspond in number and spatial arrangement so as to be useful in practicing the methods of the invention.

Similarly, the number of openings 24 of transfer plate 22 will depend in part on the number and spatial arrangement of the plurality of culture insert assemblies 52 of the transwell-like type insert plate 42 so as to be useful in practicing the methods of the invention.

The transwell-like type insert plate 42 is only partially illustrated in FIGS. 2A, 2B, 3A, 3B, 4A, and 4B to illustrate features of the invention, namely a culture insert that comprises an assembly, including a removably attachable culture surface element. FIGS. 2A, 2B, 3A, 3B, 4A, and 4B are enlarged, perspective views of a culture insert assembly 52 of the invention. The culture insert assembly 52 comprises a culture insert body 53 and a removably attachable culture surface element 55. The culture insert body 53 comprises a tubular or cylindrical side wall comprising an inner surface 51 and an outer surface 54 and extending from a first end 56 to a second end 57, and having a first opening 82 at the first end, and a second opening 84 at the second end. FIGS. 2A & 2B, FIGS. 3A & 3B, and FIGS. 4A & 4B, show that culture surface element 55 is a movable unit; i.e., culture surface element 55 can be removably attached to culture insert body 53 in forming a culture insert assembly 52 of the invention (FIG. 2B, FIG. 3B, FIG. 4B), or culture surface element 55 may be detached from culture insert body 53 (FIG. 2A, FIG. 3A, FIG. 4A) for facilitating various manipulations involving the culture surface element apart from the transwell-like type insert plate. Culture surface element 55 comprises a ring-shaped structure having a cylindrical sidewall comprising an inner surface 94 and an outer surface 95 and extending from a first end 96 (upper end) to a second end 97 (lower end), and having a first opening 92 at the first end, and a second opening at the second end which is covered by microporous matrix 98.

Figure 2A:
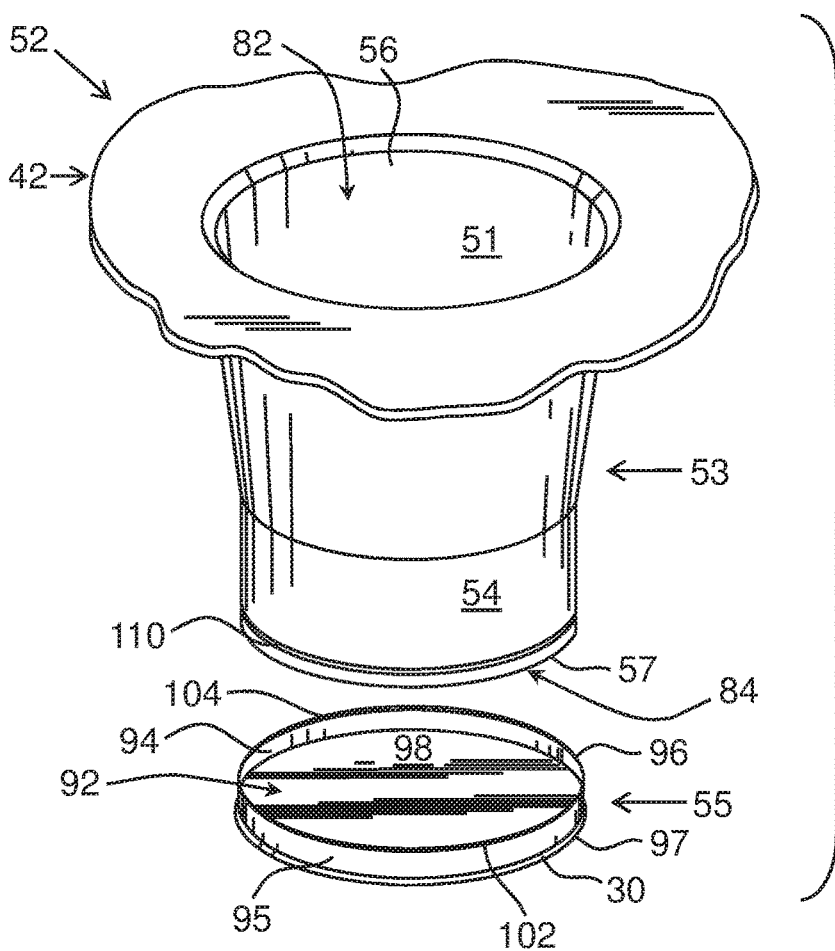
FIGS. 2A & 2B show an expanded view of a culture insert assembly according to one aspect of the invention.
Figure 2B:
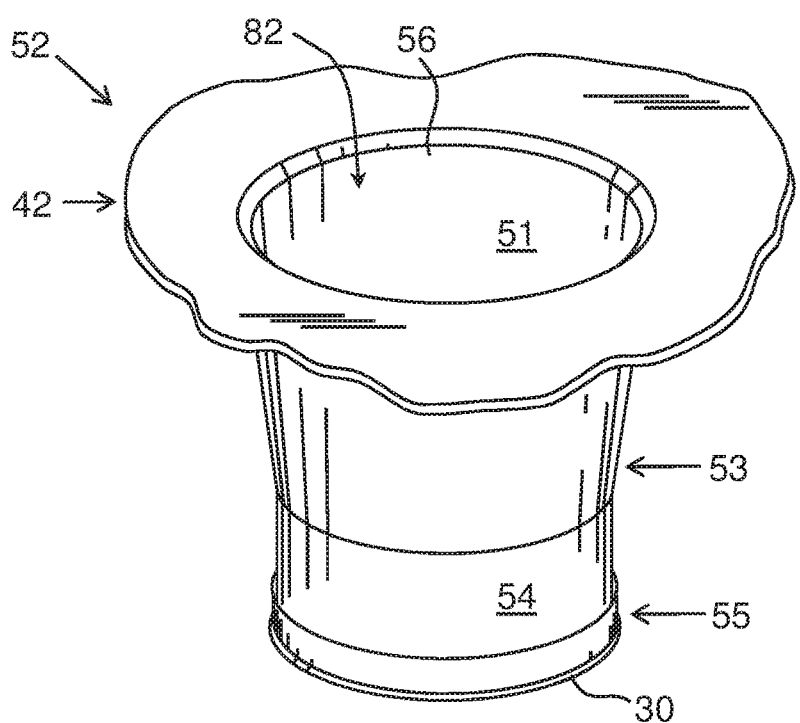
Figure 3A:
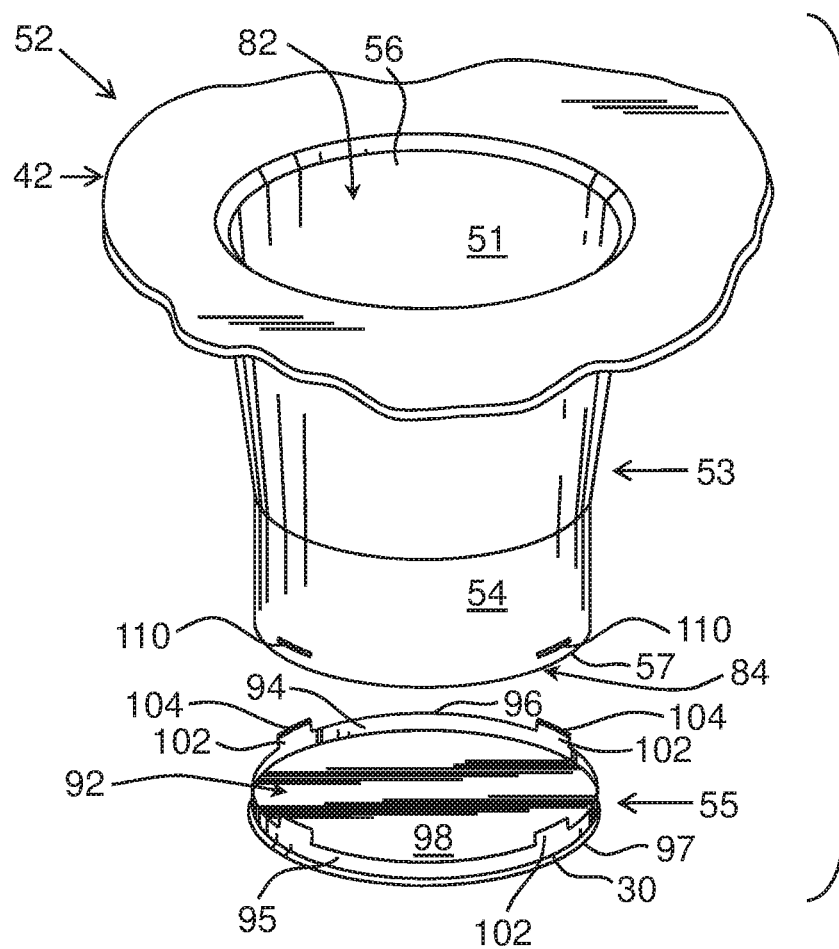
FIGS. 3A & 3B show an expanded view of a culture insert assembly according to another aspect of the invention.
Figure 3B:
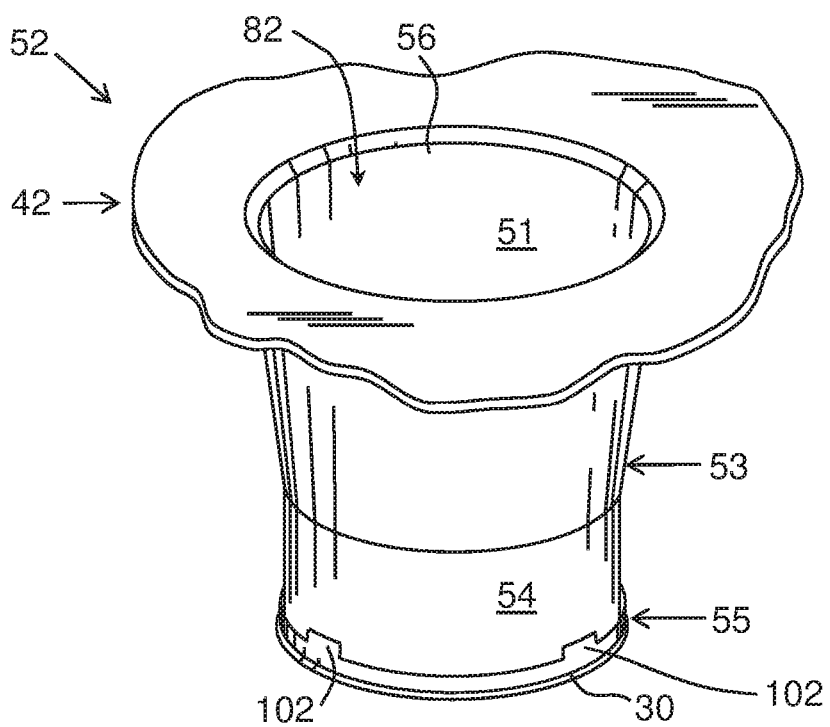

Culture surface element 55 may be removably attached to culture insert body 53 utilizing one or more attachment elements. In one aspect of the invention, culture surface element 55 comprises one or more attachment elements 102, and culture insert body 53 comprises one or more attachment elements 110 adapted to removably fixedly receive the one or more attachment elements 102 of culture surface element 55. FIG. 2A shows culture surface element 55 comprising an attachment element 102 that comprises a top annular flange or lip 104 extending inwardly from, and along a rim comprising first end 96. Attachment element 110 comprises an annular groove, which is defined in the outer wall 54 of culture insert body 53, to receive and fixedly removably engage flange 104 of attachment element 102 such that culture surface element 55 becomes removably attached to culture insert body 53 in forming culture insert assembly 52, the resultant culture insert assembly 52 being shown in FIG. 2B. In another aspect of the invention, as shown in FIG. 3A, the culture surface element 55 comprises attachment element 102, wherein attachment element 102 comprises a plurality of circumferentially-spaced arms extending upwardly from and along first end 96; wherein an attachment element 102 comprises a top annular flange or lip 104 extending inward; and wherein attachment element 110 comprises a plurality of circumferentially-spaced grooves, defined in the outer wall 54 of culture insert body 53, the grooves spaced correspondingly around the outer wall to receive and fixedly removably engage the lips 104 of the plurality of arms, such that culture surface element 55 becomes removably attached to culture insert body 53 in forming culture insert assembly 52, the resultant culture insert assembly 52 being shown in FIG. 3B. In an aspect wherein attachment element 110 comprises one or more grooves, the one or more grooves may be adapted to receive an angled lip 104 of attachment element 102 in snap-fit cooperation between angled lip 104 with the one or more grooves in removably attaching culture surface element 55 to culture insert body 53.

Figure 4A:
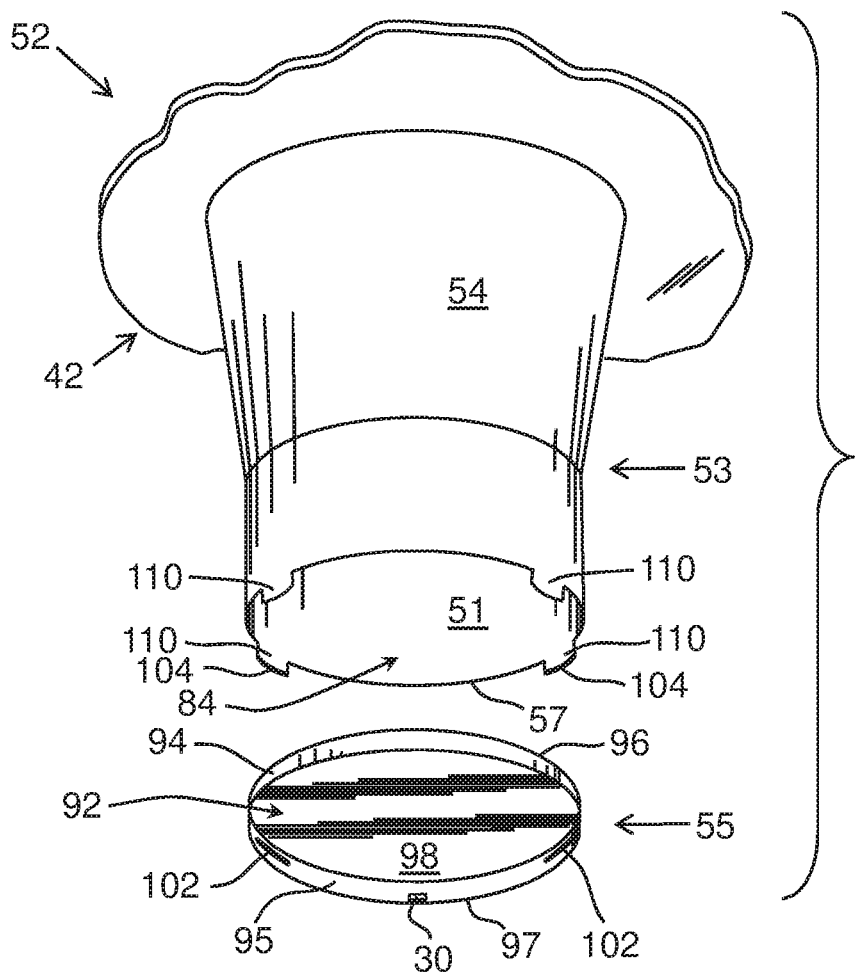
FIGS. 4A & 4B show an expanded view of a culture insert assembly according to yet another aspect of the invention.
Figure 4B:
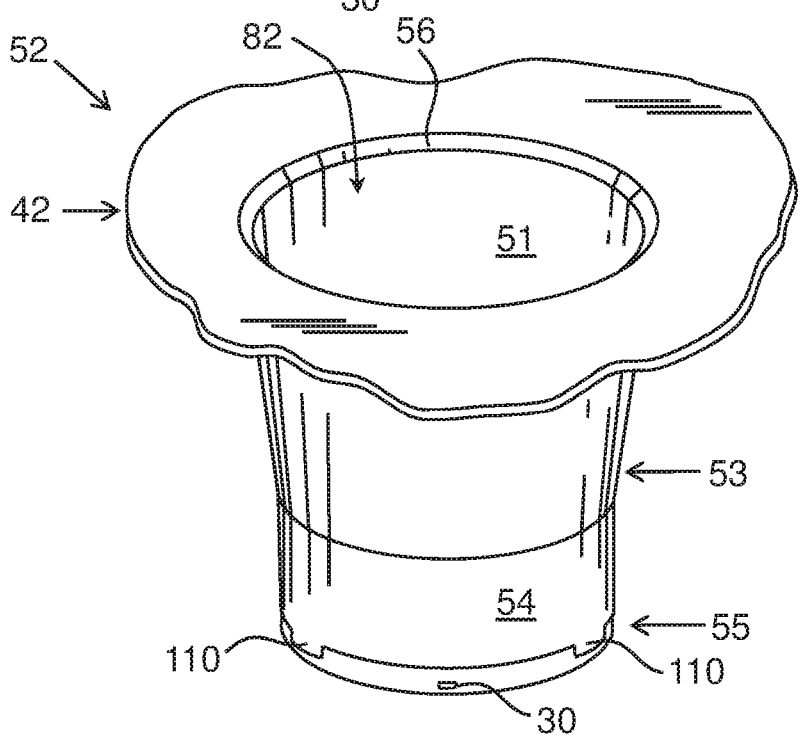

In another aspect of the invention, as shown in FIG. 4A, the culture surface element 55 comprises attachment element 102, wherein attachment element 102 comprises a plurality of circumferentially-spaced grooves, defined in the outer surface 95 of culture surface element 55; and wherein attachment element 110 comprises a plurality of circumferentially-spaced arms extending downwardly from and along the rim comprising second end 57, and wherein an attachment element 110 further comprises an annular flange or lip 104 extending inwardly and along the tip of the extended arm of attachment element 110; and wherein the grooves are spaced correspondingly around the outer surface to receive and fixedly removably engage the lips of the plurality of extended arms, such that culture surface element 55 becomes removably attached to culture insert body 53 in forming culture insert assembly 52, the resultant culture insert assembly 52 being shown in FIG. 4B. In an aspect wherein attachment element 102 comprises one or more grooves, the one or more grooves may be adapted to receive an angled lip 104 of attachment element 110 in snap-fit cooperation between angled lip 104 with the one or more grooves in removably attaching culture surface element 55 to culture insert body 53.

Figure 5:
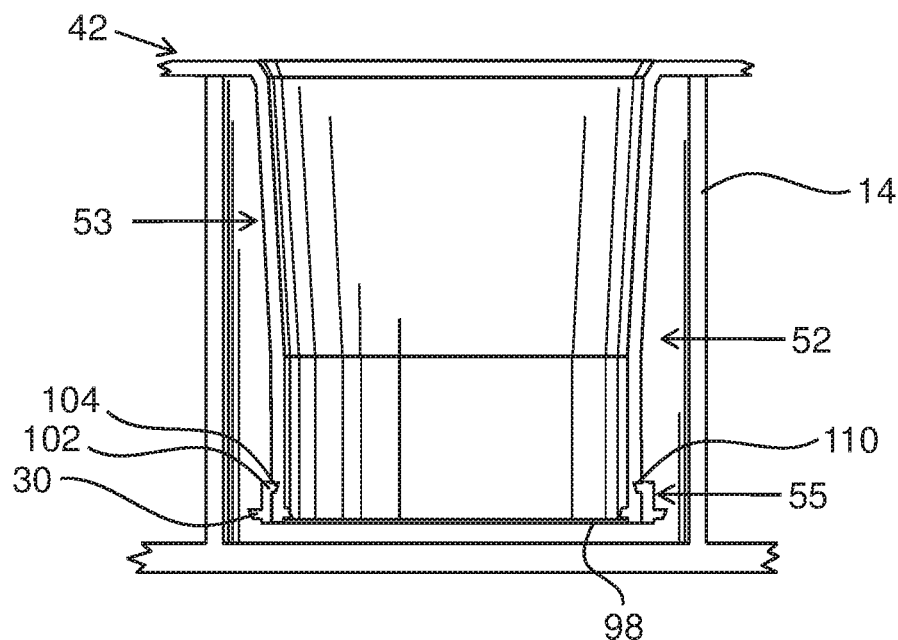
FIG. 5 is a cross-sectional view of one aspect of a culture insert assembly of the invention inserted into a multiwell plate.

FIG. 5 is a cross-sectional view of a culture insert assembly 52 of transwell-like type insert plate 42 of FIG. 1B, wherein culture insert assembly 52 is inserted into a well 14 of multiwell plate 12 (showing enlarged view of both the culture insert assembly and the well). Flange 104 of attachment element 102 is received by annular groove comprising attachment element 110 such that attachment element 102 is fixedly removably engaged with attachment element 110; wherein culture insert assembly 52 is comprised of culture surface element 55 removably attached to culture insert body 53. Microporous matrix 98 is illustrated as being extended inside culture surface element 55.

In one aspect of the invention, as shown in FIGS. 10, 11, 12, and 13, transfer plate 22 comprises: a plurality of openings 24 substantially extending and positioned along the length of transfer plate 22; a plurality of guiding elements 26 positioned along the length of transfer plate 22. In this aspect, the plurality of guiding elements 26 comprise guiding slots comprising slot-shaped openings respectively formed on the pair of wall portions 18 defining the length of each opening 24, wherein the guiding elements 26 are spaced apart and spatially arranged along the length of each opening 24 such that they form opposing pairs of guiding elements 26 along the length of each opening 24. A guiding element 26 may further comprise a recess or groove 28 formed in a wall portion 18 in forming a track or channel extending from a guiding slot and along a portion of a length of wall portion 18. Guiding elements 26 may vary in shape and dimension to correspond to, and to receivingly engage, engagement elements 30 of culture surface element 55. Optionally, in an aspect wherein transfer plate 22 comprises an open end and a closed end, provided is a capping element 140 which can be secured to the open end of transfer plate 22 to prevent culture surface elements 55 from exiting or backing out of guiding elements 26 (an optional aspect illustrated in FIGS. 8, 10, 11, 12, & 13). Capping element 140 may be in the form of an end cap, end clip, end plug or other capping element for closing off an open end of transfer plate 22 and for limiting movement of a culture surface element 55 received by, and removably fixedly engaged by, guiding elements 26, of transfer plate 22. It will be appreciated that the number of openings 24, and guiding elements 26 of transfer plate 22 will depend in part on the number and spatial arrangement of a plurality of culture surface elements 55 to be removably fixedly engaged by transfer plate 22.

Figure 7:
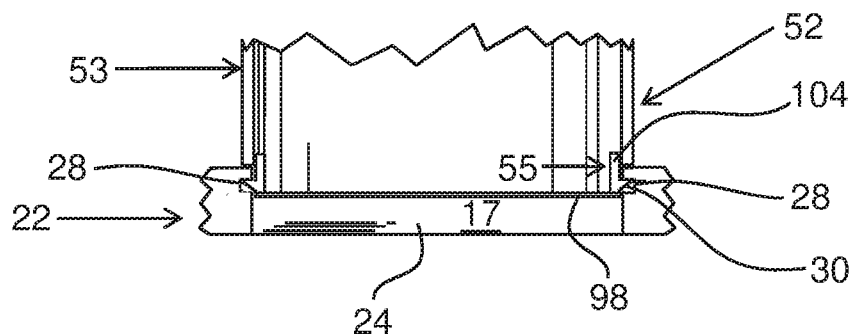
FIG. 7 is a cross-sectional view of another aspect of a culture insert assembly of the invention removably secured to a transfer plate of the invention.
Figure 10:
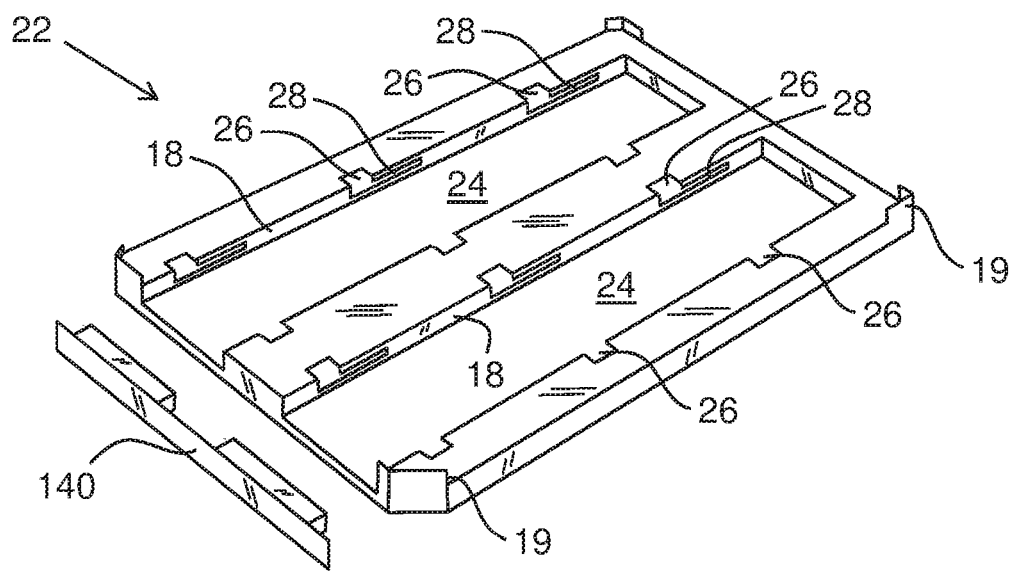
FIG. 10 is a perspective view of a transfer plate according to another aspect of the invention.

Culture surface element 55 comprises one or more engagement elements 30. As shown in FIGS. 4A and 4B, in one aspect of the invention, a plurality of engagement elements 30 are protrusions that extend outward from outer surface 95, and may comprise one or more raised ribs, tabs, ledges, or other engagement elements that fit into or onto corresponding guiding elements 26 of transfer plate 22. The engagement elements 30 may comprise a pair of diametrically opposed protrusions. In a method of the invention, partially illustrated in FIG. 11, when it is desirable to remove culture surface elements 55 from transwell-like type insert plate 42 (e.g., to facilitate imaging of cells or tissue cultured on microporous matrix 98), transwell-like type insert plate 42 comprised of a plurality of culture insert assemblies 52 are vertically aligned with and contacted with transfer plate 22 comprised of a plurality of openings 24. In this regard, culture insert assemblies 52 of transwell-like type insert plate 42 are placed in vertical alignment with corresponding openings 24 of transfer plate 22, and engagement elements 30 of culture surface elements 55 are vertically aligned with, and to be receivingly engaged by, guiding elements 26. A pair of diametrically opposed engagement elements 30 are movably inserted into a pair of opposing guiding elements 26 vertically aligned with the pair of engagement elements 30, and then engagement elements 30 are contacted and engaged with guiding elements 26. Engagement elements 30 may be further extended along guiding elements 26 by sliding engagement elements 30 along tracks 28 until engagement elements 30 are removably fixedly engaged in guiding elements 26 (e.g. by a connecting element such as tracks 28 tapering to a point distal from guiding slots such that engagement elements 30 and tracks 28 form a friction fit arrangement, or there is a groove, slot, wedge, mechanical connector, or by or in conjunction with capping element 140 or other connecting element to further facilitate removably and fixedly securing the culture surface element 55 to transfer plate 22). In one aspect of the invention, when culture surface element 55 is removably and fixedly secured to transfer plate 22, rim comprising first end 96 is flush with the top surface of transfer plate 22. In another aspect of the invention, shown in FIG. 11, it may be advantageous for various manipulations of transfer culture assembly 20 to have rim comprising first end 96 extending above the top surface of transfer plate 22. In the latter aspect, as shown in FIG. 10 in an illustrative non-limiting example, optionally, provided is one or more support elements 19 extending along and upward from the top surface of transfer plate 22 which may serve as a foot element to facilitate placement of transfer culture assembly 20 on a surface in an orientation inverted as compared to the orientation depicted in FIG. 10. For example, the orientation of the transfer culture assembly 20 may be flipped, as compared to the orientation shown in FIG. 11, such that the culture surface of microporous matrix 98 with the culture components thereon is presented in a direction facing downward and such that imaging can be accomplished using an imaging system utilizing inverted microscopy. FIG. 7 is a cross-sectional and enlarged view of a culture insert assembly 52 (as illustrated in FIG. 4B) inserted into and engaged in an opening 24 of transfer plate 22. Culture insert assembly 52 comprises culture insert body 53 and culture surface element 55 containing microporous matrix 98. A pair of diametrically opposed engagement elements 30 of culture surface element 55 are fixedly engaged in tracks 28.

Once culture surface elements 55 are fixedly secured to transfer plate 22, culture surface elements 55 are detached from the culture insert assemblies 52 by disengaging attachment elements 110 from attachment elements 102. As shown in an aspect of the invention illustrated in FIG. 11, the disengagement may be by a process comprised of one or more steps comprising pulling transwell-like type insert plate 42 in a direction away from transfer plate 22 (e.g., upward as illustrated by upward arrow in FIG. 11), pulling transfer plate 22 in a direction away from transwell-like type insert plate 42 (e.g., downward as illustrated by downward arrow in FIG. 11), or a combination thereof, with sufficient force such that attachment elements 110 are disengaged from attachment elements 102, while engagement elements 30 remain removably fixedly engaged with guiding elements 26. Thus, in this method, culture surface elements 55 are transferred from the transwell-like type insert plate 42 to transfer plate 22. A transfer plate 22, now comprising a plurality of culture surface elements 55 fixedly engaged thereto, comprises a transfer culture assembly 20. The method of the invention may further comprise subjecting (e.g., one or more of processing and analyzing) culture components (cells and/or tissues) on microporous matrices 98 of culture surface elements 55 of transfer culture assembly 20 to one or more analytical techniques known in the art. An illustrative non-limiting example of an analytical technique is an imaging technique known in the art, including using any one or more of an automated imaging system, manual imaging system, and high-throughput imaging system.

Figure 8:
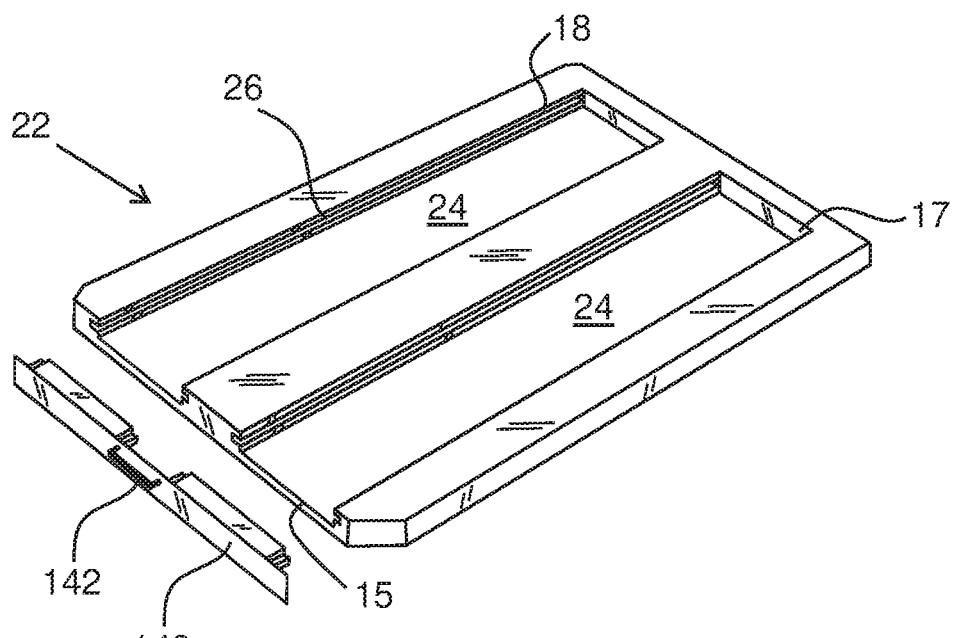
FIG. 8 is a perspective view of a transfer plate according to one aspect of the invention.
Figure 9:
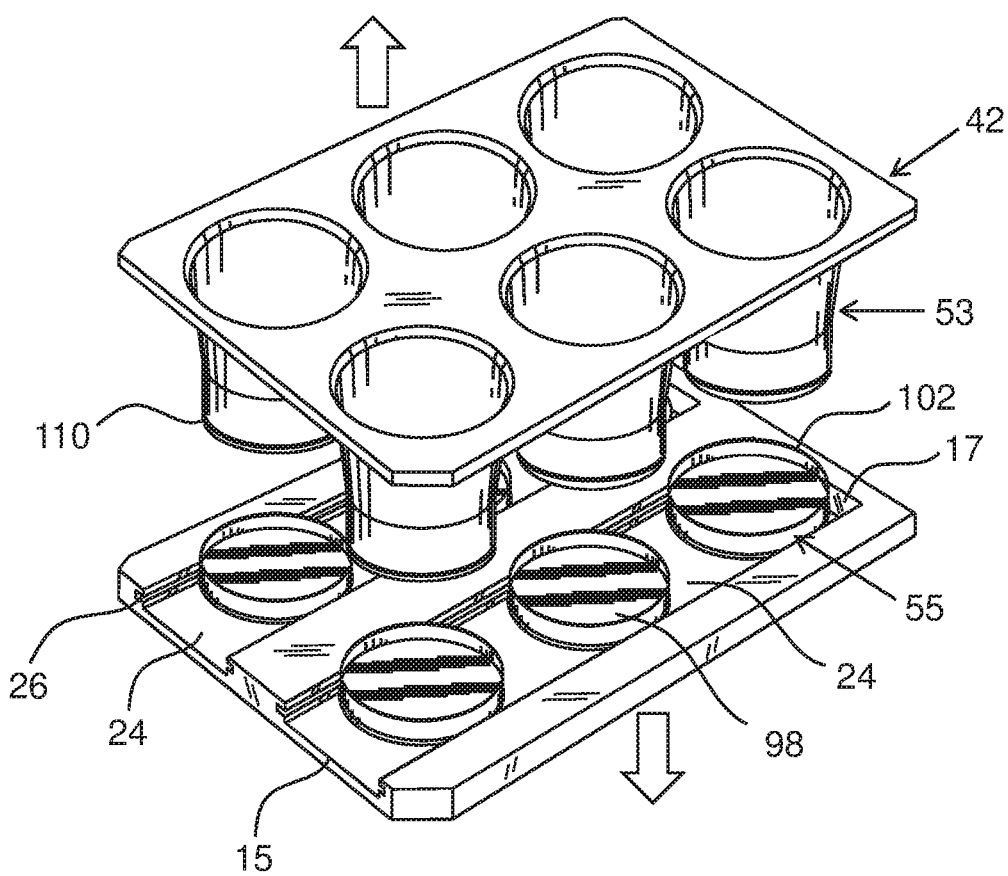
FIG. 9 is a perspective view showing transfer of culture surface elements from a transwell-like type insert plate to a transfer plate, in forming a transfer culture assembly, according to one aspect of the invention.

In another aspect of the invention, as shown in FIGS. 8 and 9, transfer plate 22 comprises a plurality of openings 24 substantially extending and positioned along the length of transfer plate 22; a plurality of guiding elements 26 comprising engagement elements are positioned along the length of transfer plate 22. In this aspect, a guiding element 26 comprises a recess or groove formed in a wall portion 18 in forming a track or channel extending substantially along the length of wall portion 18. Guiding elements 26 may vary in shape and dimension to correspond to, and to receivingly engage, engagement elements 30 of culture surface element 55. Optionally, in an aspect wherein transfer plate 22 comprises an open end 15 and a closed end 17, provided is a capping element 140 which can be secured to the open end of transfer plate 22 to prevent culture surface elements 55 from exiting or backing out of guiding elements 26. Capping element 140 may further comprise a handle element 142 to facilitate movement of the capping element 140 onto or off of open end 15.

Figure 6:
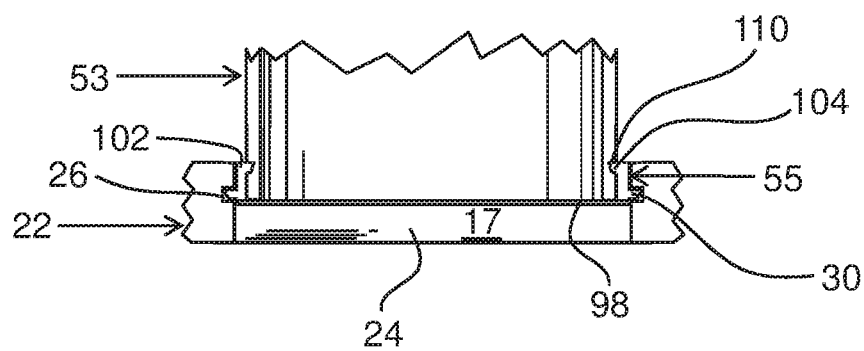
FIG. 6 is a cross-sectional view of one aspect of a culture insert assembly of the invention removably secured to a transfer plate of the invention.

Culture surface element 55 comprises one or more engagement elements 30. As shown in FIGS. 2A, 2B, 3A, and 3B, in one aspect of the invention, engagement element 30 is an annular protrusion or flange extending outward from outer surface 95 along lower end 97. In a method of the invention, partially illustrated in FIG. 9, when it is desirable to remove culture surface elements 55 from transwell-like type insert plate 42 (e.g., to facilitate imaging of cells or tissue cultured on microporous matrix 98), transwell-like type insert plate 42 comprised of a plurality of culture insert assemblies 52 is contacted with transfer plate 22 comprised of a plurality of openings 24. In this regard, engagement element 30 of culture insert assemblies 52 are placed in spatial alignment with corresponding openings 24 of transfer plate 22 to be receivingly engaged by, guiding elements 26. Each engagement element 30 is movably inserted into a pair of opposing guiding elements 26 (opposing in that they are located on opposite sides of the same opening 24), in contacting and engaging engagement element 30 with a pair of guiding elements 26. Engagement elements 30 are further extended along guiding elements 26 by sliding engagement elements 30 along tracks comprising guiding elements 26. Optionally, and if desired, engagement elements 30 may be removably fixedly engaged from further movement in guiding elements 26 by a connecting element such as a capping element 140 or other connecting element to removably and fixedly securing the culture surface element 55 to transfer plate 22. FIG. 6 is a cross-sectional and enlarged view of a culture insert assembly 52 and an opening 24 of transfer plate 22. Culture insert assembly 52 comprises culture insert body 53 and culture surface element 55 containing microporous matrix 98. Culture surface element 55 comprises an attachment element 102 comprising a top annular flange with angled lip 104 receivingly removably attached to annular groove comprising attachment element 110 (in an aspect as illustrated in FIGS. 2A and 2B). Engagement element 30 of culture surface element 55 is fixedly engaged in a pair of guiding elements 26 of transfer plate 22.

Once culture surface elements 55 are fixedly secured to transfer plate 22, culture surface elements 55 are detached from the culture insert assemblies 52 by disengaging attachment elements 110 from attachment elements 102. As shown in an aspect of the invention illustrated in FIG. 9, the disengagement may be by a process comprised of one or more steps comprising pulling transwell-like type insert plate 42 in a direction away from transfer plate 22 (e.g., upward as illustrated by upward arrow in FIG. 9), pulling transfer plate 22 in a direction away from transwell-like type insert plate 42 (e.g., downward as illustrated by downward arrow in FIG. 9), or a combination thereof, with sufficient force such that attachment elements 110 are disengaged from attachment elements 102, while engagement elements 30 remain removably fixedly engaged with guiding elements 26. Thus, in this method, culture surface elements 55 are transferred from the transwell-like type insert plate 42 to transfer plate 22 in forming a transfer culture assembly 20. The method of the invention may further comprise subjecting cells or tissues on microporous matrices 98 of culture surface elements 55 of transfer culture assembly 20 to one or more analytical techniques known in the art (e.g., biological characterization via one or more of: staining with one or more detectable molecules, imaging, and a combination thereof).

Example 1

General Description of the Culture System

The culture system 8 of the invention is provided which includes a base 12 comprising a multiwell plate for culturing cells or tissues; a transwell-like type insert plate 42 comprising a plurality of culture insert assemblies 52, wherein each culture insert assembly comprises a culture surface element that is removably mounted to a culture insert body; and a cover or lid 62 designed to fit over the transwell-like type insert plate. The culture system 8 of the invention may further comprise a transfer plate 22 comprising a plurality of openings 24. The multiwell plate comprises a plurality of openings (wells) 14 such as, for example, 2, 4, 6, 8, 12, 16, 24, 36, 48, or 96 openings, or other number as desired by a user of the system. The transfer plate comprises a plurality of openings 24 substantially extending and positioned along the length of transfer plate 22. In one aspect, the culture insert assemblies 52 of the transwell-like type insert plate 42, and the wells 14 in multiwell plate 12, would desirably correspond in number and spatial arrangement so as to be useful in practicing a method of the invention (e.g., such that the culture surface elements can be placed in the wells of the multiwell plate that align with (the wells "correspond with") the culture surface elements).

Provided is a method of culturing cells or tissues comprising the steps of: (a) providing a transwell-like type insert plate according to the invention wherein the transwell-like type insert plate comprises a plurality of culture surface elements removably attached thereto, and wherein the culture surface elements comprise a microporous matrix onto which cells or tissues can be cultured; (b) placing the cells or tissues to be cultured onto the microporous matrix of the culture surface elements; (c) providing a multiwell plate comprising a plurality of openings (wells); (d) placing the culture surface elements, removably attached to the transwell-like type insert plate, into corresponding wells of the multiwell plate, wherein the wells further comprise culture medium for culturing the cells or tissues, and wherein the culture medium contacts the microporous matrix of the culture surface elements. The wells of the multiwell plate may further comprise cells or tissue. It will be appreciated by those skilled in the art that the cells or tissues to be cultured can be deposited, layered, or otherwise placed onto the microporous matrix either prior to placing the culture surface elements into corresponding wells of a multiwell plate (e.g., in a bioprinting process), or after placing the culture surface elements into corresponding wells of a multiwell plate. Likewise, culture medium may be placed in the wells of the multiwell plate before or after placing the plurality of culture surface elements into corresponding wells of a multiwell plate.

The culture system may further include a removable lid 62. The lid comprises a top wall, and peripheral side walls that extend from the top wall. The lid removably covers the upper surface of the transwell-like type insert plate, wherein the peripheral sides of the lid abut with the sidewalls of the transwell-like type insert plate or with the sidewalls of the multiwell plate having the transwell-like type insert plate inserted therein. The lid serves to cover the surface openings in the transwell-like type insert plate, and the culture compartments extending therefrom as formed by the culture insert assembly of the invention, so that minimized is contamination or cross-contamination of cultures contained in the culture system. The culture system, and its various structural parts, may be manufactured using methods known in the art, such as standard molding techniques (e.g., injection molding), 3D printing, and the like, from a variety of materials suitable for the culture system's purpose, including, for example, one or more plastics, polymers, polybutylene, polyethylene, polystyrene, polyethylene terephthalate, polypropylene, polycarbonate, polymethyl methacrylate (PMMA), acrylonitrile butadiene styrene (ABS), and other suitable materials, or a combination thereof. The structural components of the culture system may be optically transparent, translucent or opaque. For those structural components, such as the bottom of the wells of a multiwell, or a bottom of the transfer plate (in the optional aspect wherein the transfer plate comprises a bottom surface substantially along the length and width of the transfer plate), through which cultured cells or tissues are desired to be observed, then such structural components of the culture system are desirable substantially transparent (transparent and colorless, transparent colored, or translucent). Sterilization of such components of the culture system can be done by methods known in the art, such as standard gamma radiation, or autoclaving. Some aspects of the invention, including a culture system according to the invention, utilize a multiwell plate. Multiwell plates are commercially available from manufacturers or distributers such as Corning, Millipore, and Becton-Dickinson.

Transwell-Like Type Insert Plate, and Culture Insert Assembly

Provided is a transwell-like type insert plate 42 comprising a plurality of culture insert assemblies 52, wherein an opening 82 on the upward surface of a transwell-like type insert plate forms the opening of a culture insert assembly. Unlike conventional transwell insert plates, the transwell-like type insert plate of the invention comprises a plurality of movable units that can be removed or disengaged from the transwell-like type insert plate by a transfer plate 22. The movable units comprise culture surface elements 55 that may be provided in a form as removably attached to the transwell-like type insert plate (see, e.g., FIGS. 1, 2B, 3B, and 4B), or in a form as removably attached to a transfer plate (see, e.g., FIGS. 9 & 11). Culture surface elements are removably attached to culture insert bodies 53 in forming culture insert assemblies. The culture insert bodies are an integral element of the transwell-like type insert plate (e.g., formed as an inseparable portion of the transwell-like type insert plate in the manufacture of the transwell-like type insert plate). In one aspect, each culture insert body comprises cylindrical vertical walls defining a tubular structure with two openings 82 & 84, defining the opposing ends of the tubular structure. For example, an upper end 82 of the culture insert body defines an opening in the transwell-like type insert plate, and a lower end 84 defines a bottom opening which is opposite to the opening at the surface of the transwell-like type insert plate. A detachable or movable unit comprising a culture surface element may be removably attached to the lower end of the tubular culture insert body in providing a bottom surface to the culture insert body, forming a compartment for culturing, and forming a culture insert assembly of the invention.

Desirably, removably attaching the culture surface element to the culture insert body forms a leak-proof or substantially leak-proof arrangement such that when a culture inset assembly is aligned and inserted into a well of a multiwell plate (e.g., see FIG. 5) that exchange of fluid components or fluid content between the culture medium and the culture components (e.g., cells or tissue cultured on the surface of microporous matrix 98 of a culture surface element) is substantially through the pores or via the porosity of microporous matrix 98 in contact with the culture medium contained in the well of the multiwell plate. Optionally, a sealing element (e.g., O-ring, silicone gasket, and the like) may be disposed between the culture insert body and culture surface element to facilitate the leak-proof arrangement. A culture surface element may generally be ring-shaped structure with a cylindrical sidewall and an upper opening 96 and lower opening 97. The lower opening of the sidewall may have a flange extending from the inner surface of the sidewall so as to provide an edge to which may be fixed the microporous matrix. Alternatively, the microporous matrix may be fixed to the sidewall. The microporous matrix may be fixed either on an outside surface of the culture surface element (see, e.g., FIG. 6) or an inside surface of culture surface element (see, e.g., FIG. 5). Fixing a microporous matrix to a surface of the culture surface element may be by heat fixing, pressure fit (e.g. between a sealing element and the surface to which it is fixed), an adhesive, or by other means known in the art.

Materials which may be utilized for the microporous matrix may comprise a porous material that includes, but is not limited to, a polymer, nylon, polyester, polycarbonate, polyethylene terephthalate, hydrated gel, polyethylene, polytetrafluoroethylene, and the like. The microporous matrix may be transparent or translucent to facilitate imaging of cells or tissues cultured on the surface of the microporous matrix. The material comprising the microporous matrix is of a sufficient porosity to allow the passage of macromolecules, proteins, ions, and nutrients from culture medium to cross the microporous matrix and contact cells or tissues deposited on a surface (culture surface) of the microporous matrix, while preventing direct cell to cell contact between cells or tissues cultured on the microporous matrix in the culture insert with cells cultured in the corresponding well of a multiwell plate containing culture medium. Additionally, the surface of the microporous matrix may be treated or coated to facilitate culture of cells or tissues. In one aspect, the microporous matrix may be etched or activated (e.g., plasma-treated) to alter the electrical charge of certain regions of the surface of the microporous matrix on which cells or tissues are to be cultured. In another aspect, one or more biological components may be used to treat or coat all or a portion of the surface of a microporous matrix. Such biological components may include, but are not limited to, one or more growth factors, biomatrix such as extracellular matrix, laminin, fibronectin, collagen, elastin, gelatin, hyaluronectin, chondronection, osteopontin, fibrillin, sialoprotein, tenascin, proteoglycans, other proteins, glycoproteins, peptides, carbohydrates, and a combination thereof.

Transfer Plate and Transfer Culture Assembly

The design of the culture insert assembly 52 and the transfer plate 22 allows for the culture surface element 55 to be a movable unit. This design allows for processes for manipulation of the cell culture surface element. In one example, a plurality of the movable units, each movable unit comprising a culture surface element and its supporting structure (together a "culture surface assembly") are initially separated from the corresponding culture inserts, but are removably attached to the transfer plate through engagement of one or more engagement elements 30 of each culture surface element with one or more guiding elements 26 of a transfer plate in forming a transfer culture assembly 20. Thus, in one aspect of the invention, provided is a transfer culture assembly comprising a plurality of cell surface elements removably attached to a transfer plate. The transfer culture assembly may further comprise one or more culture components deposited on or applied on (in contact with) the micropororous matrix of one or more of the plurality of culture surface elements.

In one illustration of using the transfer culture assembly, the transfer plate may have one or more alignment elements (e.g., recesses, groove, clip, protrusion, tab, and the like) along and integrated as part of its base such that an automated handling system may mechanically receive the transfer plate. In the automated process, one or more culture components comprised of one or more cell types, biological components (e.g., one or more growth factors, biomatrix (e.g., extracellular matrix or components thereof such as laminin, fibronectin, collagen, elastin, gelatin, hyaluronectin, chondronection, osteopontin, fibrillin, sialoprotein, tenascin, proteoglycans, and a combination thereof) proteins, and the like) and a combination thereof, may be contacted with (applied directly onto or layered onto) a microporous matrix in each culture surface element of the transfer culture assembly selected for use. One example of this process is bioprinting of cells or tissue for subsequent culturing. Following the application of one or more culture components to the transfer culture assembly, the transfer culture assembly may be removed from the automated handling system, and stored and/or transported for further use. For example, the transfer culture assembly may be sealed in a container for transport and/or storage. In one example, the container also contains a liquid medium for support and/or maintenance of viability of the cells or tissues ("support medium") deposited in the transfer culture assembly. The support medium will depend on the cell or tissue type to be maintained. Culture components may comprise cells or tissues comprising human cells or tissues, mammalian cells or tissues, insect cells or tissues, plant cells or tissues, cell lines, transformed cells, transfected cells, genetically modified cells, and combinations thereof. Commercially available culture media may be used for this purpose. As known to those skilled in the art, non-limiting examples include RPMI Media 1640, Dulbecco's Modified Eagle Medium (DMEM), DMEM: Nutrient Mixture F-12 (DMEM/F12), Minimum Essential Media (MEM), RF-10 medium, IMDM and the like, with supplementation with serum or a serum substitute, as required by the cell type or tissue type to be maintained. While the container may be comprised of any suitable material for transport and/or storage, in one aspect the container comprises a pouch or bag having at least one surface which comprises a gas permeable, liquid impermeable membrane ("gas permeable membrane"). This gas permeable membrane allows for the transfer of gases to contribute to the support and/or maintenance of the cells or tissues contained in the transfer culture assembly in contact with the support medium and sealed within the container. Thickness of the gas permeable membrane will depend on the desired resultant characteristics which may include, but are not limited to, structural integrity, degree of gas permeability, and rate of transfer of gases. In general, the thickness of a gas permeable membrane can range from less than about 0.00125 inches to about 0.005 inches. In a preferred embodiment, the thickness of the membrane is in the range of about 0.002 inches to about 0.004 inches, and in a more preferred embodiment, 0.004 inches. The gas permeable membrane may be comprised of one or more membranes known in the art. As known to those skilled in the art, non-limiting examples include a membrane comprised of a suitable polymer, such polystyrene, polyethylene, polycarbonate, polyolefin, ethylene vinyl acetate, polypropylene, polysulfone, polytetrafluoroethylene, or a silicone copolymer. For transport, the pouch or bag comprising the transfer culture assembly and support medium may be sealed in a leak proof arrangement (e.g., heat sealed, zipper closure, and the like) and then placed in a container of suitable rigidity (e.g., comprised of cardboard, paperboard, Styrofoam, and the like) for shipping.

In an alternative example of subsequent use of a transfer culture assembly, following deposition of the one or more culture components, either manually or using an automated handling system, a process comprises spatially aligning the transfer culture assembly with the transwell-like type insert plate of the invention such that (a) each culture surface element of a plurality of culture surface elements is spatially aligned with a corresponding culture insert body of a plurality of culture insert bodies, (b) facilitated is contact between one or more attachment elements of each culture surface element of a plurality of culture surface elements with one or more attachment elements of a corresponding culture insert body of a plurality of culture insert bodies, such that the plurality of culture surface elements become removably attached to the plurality of culture insert bodies through contact and engagement of the respective attachment elements, in forming culture insert assemblies, and (c) detaching the culture surface elements from the transfer culture assembly by disengaging the engagement elements of the culture surface elements from the guiding elements of the transfer plate, thereby resulting in a transfer plate, and the transwell-like type insert plate of the invention now comprising a plurality of culture insert assemblies (i.e., the plurality of movable units (culture surface elements) are transferred from the transfer plate to the transwell-like type insert plate). The method may further comprise spatially aligning and inserting the plurality of culture insert assemblies, of a transwell-like type insert plate comprising a plurality of culture insert assemblies, into corresponding openings or wells of a multiwell plate in forming a culture system of the invention for subsequent culturing of the cells or tissues contained therein, and may further comprise subsequent analyses performed on the cultured cells or tissues.

Regarding subsequent analyses performed on cells or tissue cultured in a culture system of the invention, a method is provided wherein culture surface elements are transferred from the transwell-like type insert plate to the transfer plate. The method comprises (a) aligning the plurality of culture insert assemblies containing culture components comprised of cultured cells or cultured tissue, of a transwell-like type insert plate comprising a plurality of culture insert assemblies, with corresponding openings of a transfer plate (b) contacting one or more engagement elements of each culture surface element, of the plurality of culture surface elements, with one or more guiding elements associated with a corresponding opening of a transfer plate, such that the plurality of culture surface elements become removably attached to the transfer plate through engagement of the engagement elements of the culture surface elements, of the plurality of culture surface elements, with the guiding elements of the transfer plate, and (c) detaching the plurality of culture surface elements from the culture insert assemblies of the transwell-like type insert plate by disengaging the attachment elements of the plurality of culture surface elements from the attachment elements of the transwell-like type insert plate, thereby resulting in a transfer plate now comprising a plurality of culture insert assemblies (transfer culture assembly), and the transwell-like type insert plate of the invention lacking culture surface elements (i.e., the plurality of movable units (culture surface elements) are transferred from the transwell-like type insert plate to the transfer plate). The method further comprises analyzing the cells or tissues by one or more imaging techniques known in the art, including using automated imaging systems, manual imaging systems, and high-throughput imaging systems.

Figure 11:
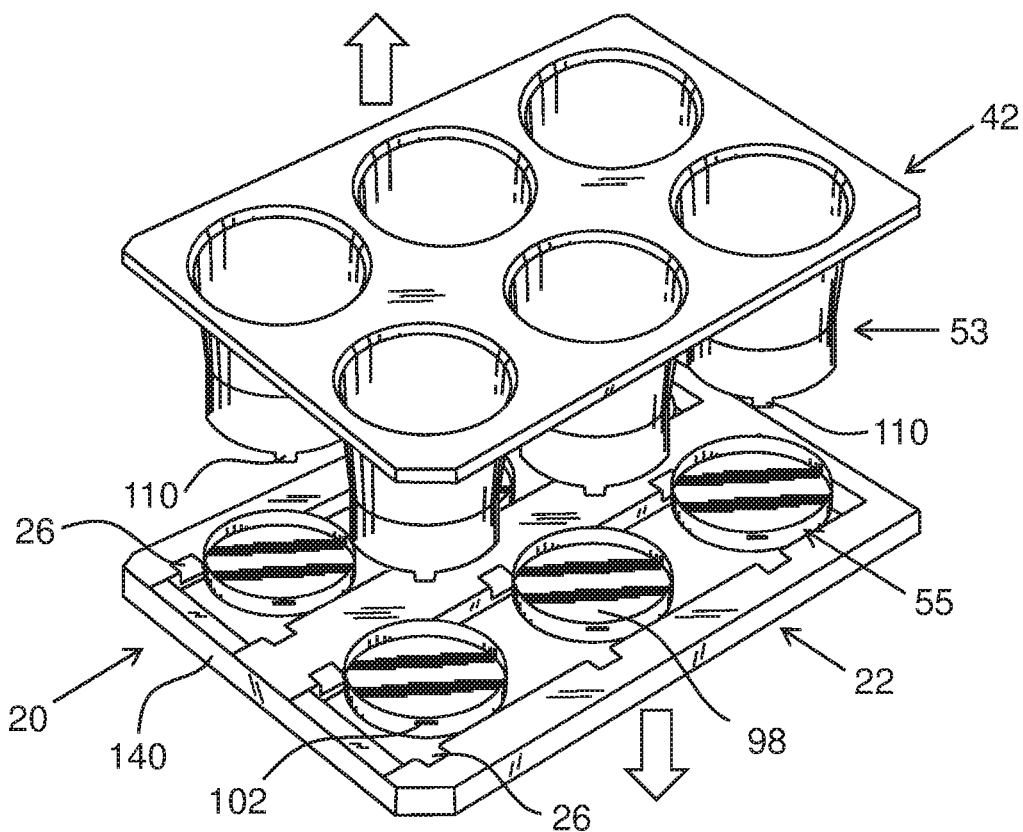
FIG. 11 is a perspective view showing transfer of culture surface elements from a transwell-like type insert plate to a transfer plate, in forming a transfer culture assembly, according to one aspect of the invention.
Figure 12:
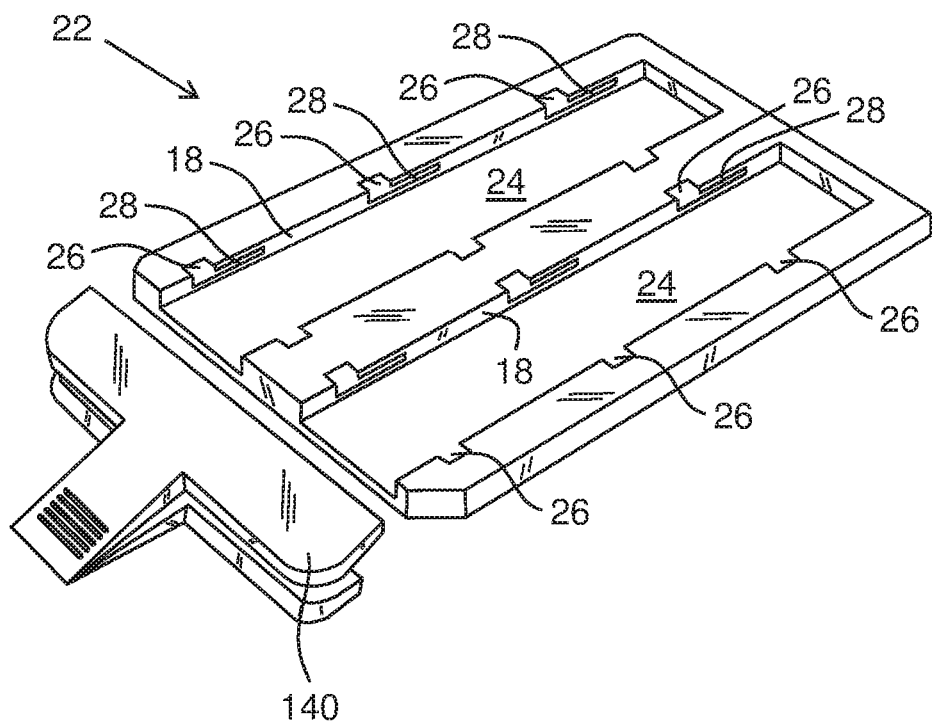
FIG. 12 is a perspective view of a transfer plate according to yet another aspect of the invention.
Figure 13:
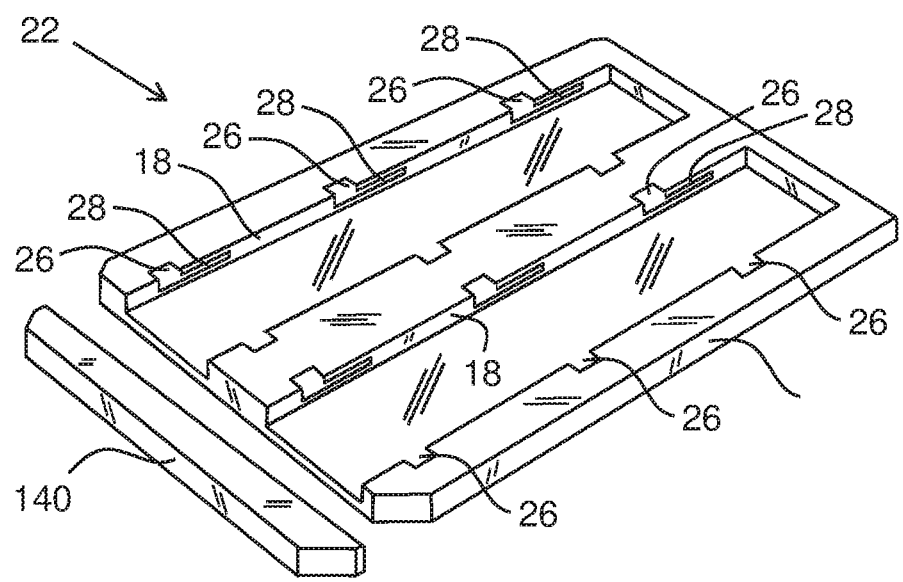
FIG. 13 is a perspective view of a transfer plate according to a further aspect of the invention.

With the plurality of culture surface elements removably attached to the transfer plate, an advantage of the transfer culture assembly of the invention is that it may be subject to further analysis in at least 2 orientations. In one orientation, the transfer culture assembly presents the culture surface with the culture components thereon in a direction facing upward such that imaging can be accomplished using an imaging system utilizing upright microscopy (see. e.g., FIGS. 9 & 11). In another aspect of the invention, the orientation of the transfer culture assembly is flipped, as compared to the previously described orientation (e.g., such that the culture surfaces of the microporous matrices, with the culture components thereon, are presented in a direction facing downward; for purposes of reference, a downward direction is indicated by downward facing arrow at the bottom of FIG. 11) so that imaging can be accomplished using an imaging system utilizing inverted microscopy. To facilitate imaging of culture components present in a transfer culture assembly, in one aspect of the invention as illustrated in FIGS. 11 & 12, the transfer plate lacks a bottom surface for covering openings 24. An additional step in the method is to treat the culture components (cells or tissues cultured or applied on the surface of microporous matrix of culture surface elements) with one or more detector molecules comprising a targeting molecule (e.g., antibody, antibody fragment, peptide, protein, aptamer, nucleic acid molecule, substrate (protein or carbohydrate), enzyme, and the like) labeled with a detector molecule (luminescent molecule, fluorescent molecule, bioluminescent molecule, enzyme substrate, quantum dots, and the like), the signals from which may be easily detected and quantified with any one of a variety of automated and/or high-throughput instrumentation systems including fluorescence multi-well plate readers, and automated cell-based imaging systems that provide spatial resolution of the signal.

What is claimed is:

1. A culture system comprising: a base comprising a multiwell plate; an insert plate comprising a plurality of culture insert assemblies which are integrally formed as part of the insert plate, wherein each culture insert assembly comprises a culture surface element that is removably mounted to a culture insert body; a transfer plate comprised of a plurality of openings for engaging a plurality of culture surface elements for facilitating transfer of culture surface elements between an insert plate and the transfer plate; wherein a culture surface element comprises one or more engagement elements to contact and be receivingly engaged by the transfer plate; and a removable lid.

2. The culture system of claim 1, wherein the culture insert assemblies of the insert plate correspond in number and spatial arrangement to that of the wells in the multiwell plate.

3. The culture system of claim 1, wherein each culture surface element comprises a microporous matrix.

4. The culture system of claim 3, wherein the microporous matrix further comprises one or more culture components.

5. The culture system of claim 1, wherein the transfer plate lacks a bottom surface covering the plurality of openings.

6. The transfer plate of claim 1, wherein the culture system lacks a bottom surface covering the plurality of openings.

7. A method for transferring a plurality of culture surface elements, from an insert plate comprising a plurality of culture insert assemblies, to a transfer plate, the method comprising (a) aligning the plurality of culture insert assemblies containing culture components comprised of cultured cells or cultured tissue, of an insert plate comprising a plurality of culture insert assemblies, with corresponding openings of a transfer plate; (b) contacting one or more engagement elements of each culture surface element, of the plurality of culture surface elements, with one or more guiding elements associated with a corresponding opening of a transfer plate, such that the plurality of culture surface elements become removably attached to the transfer plate through engagement of the engagement elements of the culture surface elements, of the plurality of culture surface elements, with the guiding elements of the transfer plate and (c) detaching the plurality of culture surface elements from the culture insert assemblies of the insert plate by disengaging attachment elements of the plurality of culture surface elements from attachment elements of the insert plate, thereby resulting in a transfer plate now comprising a plurality of culture insert assemblies, and the insert plate lacking culture surface elements.

8. The method of claim 7, wherein a culture surface element further comprises a microporous matrix and one or more culture components.

9. A culture system comprising: a base comprising a multiwell plate; an insert plate comprising a plurality of culture insert assemblies which are integrally formed as part of the insert plate, wherein each culture insert assembly comprises a culture surface element that is removably mounted to a culture insert body through one or more attachment elements of the culture insert body removably fixedly received by one or more attachment elements of a culture surface element, wherein an opening in the insert plate is formed by an opening of a culture insert assembly, and wherein a culture surface element comprises a microporous matrix and one or more engagement elements to contact and be receivingly engaged by a transfer plate; a removable lid; and a transfer plate comprised of a plurality of openings for engaging a plurality of culture surface elements.

10. The culture system of claim 9, wherein the culture insert assemblies of the insert plate correspond in number and spatial arrangement to that of the wells in the multiwell plate.

11. The culture system of claim 9, wherein the culture insert assemblies of the insert plate correspond in number and spatial arrangement to that of the plurality or openings of which the transfer plate is comprised.

12. The culture system of claim 9, wherein the transfer plate lacks a bottom surface covering the plurality of openings.

13. The culture system of claim 9, wherein the microporous matrix further comprises one or more culture components.

14. A culture system comprising: an insert plate comprising a plurality of culture insert assemblies which are integrally formed as part of the insert plate, wherein an opening in the insert plate is formed by an opening of a culture insert assembly, where a culture insert assembly comprises a culture surface element removably attached to a culture insert body through one or more attachment elements of the culture insert body removably fixedly received by one or more attachment elements of a culture surface element, and wherein a culture surface element comprises a microporous matrix and one or more engagement elements to contact and be receivingly engaged by a transfer plate; and a transfer plate comprised of a plurality of openings corresponding in number and spatial arrangement to that of the plurality of culture insert assemblies of the insert plate, and wherein the transfer plate lacks a bottom surface covering the plurality of openings.

15. The culture system of claim 14, further comprising one or more of (a) a multiwell plate, and (b) a removable lid.

16. The culture system of claim 14, wherein the microporous matrix further comprises one or more culture components.

17. A method for transferring a plurality of culture surface elements from a transfer culture assembly to an insert plate; wherein the insert plate comprises a plurality of culture insert bodies, with one or more attachment elements of a culture insert body to be received by one or more attachment elements of a culture surface element; wherein the transfer culture assembly comprises a plurality of culture surface elements removably attached to a transfer plate, the method comprising: (a) spatially aligning the plurality of culture insert bodies of the insert plate with the plurality of culture surface elements removably attached to the transfer plate so that each culture surface element of a plurality of culture surface elements is spatially aligned with a corresponding culture insert body of a plurality of culture insert bodies, (b) contacting one or more attachment elements of each culture surface element of a plurality of culture surface elements with one or more attachment elements of a corresponding, spatially aligned culture insert body of a plurality of culture insert bodies, such that the plurality of culture surface elements become removably attached to the plurality of culture insert bodies through contact and engagement of the respective attachment elements, in forming culture insert assemblies, and (c) detaching the culture surface elements from the transfer culture assembly in disengaging the culture surface elements from the transfer plate; thereby transferring a plurality of culture surface elements from the transfer culture assembly to the insert plate.

\* \* \* \* \*